United States Patent
Kim et al.

(10) Patent No.: US 10,894,104 B1
(45) Date of Patent: Jan. 19, 2021

(54) LED LIGHTING DEVICE FOR STERILIZING SURFACE OR SPACE

(71) Applicant: PSYCURE CO., LTD., Seoul (KR)

(72) Inventors: Hyun-Jeong Kim, Seoul (KR); Sang-Ho Jung, Incheon (KR)

(73) Assignee: PSYCURE CO., LTD., Seoul (KR)

( * ) Notice: Subject to any disclaimer, the term of this patent is extended or adjusted under 35 U.S.C. 154(b) by 0 days.

(21) Appl. No.: 17/032,769

(22) Filed: Sep. 25, 2020

(30) Foreign Application Priority Data

Sep. 11, 2020 (KR) .......................... 10-2020-0116840

(51) Int. Cl.
*A61L 2/10* (2006.01)
*A61L 9/20* (2006.01)

(52) U.S. Cl.
CPC .. *A61L 2/10* (2013.01); *A61L 9/20* (2013.01)

(58) Field of Classification Search
None
See application file for complete search history.

(56) References Cited

U.S. PATENT DOCUMENTS

| | | | | |
|---|---|---|---|---|
| 9,698,544 B2* | 7/2017 | Wu | ...................... | H01R 13/6658 |
| 2007/0003430 A1* | 1/2007 | Kaiser | ................. | A61M 1/3683 |
| | | | | 422/24 |
| 2008/0080175 A1* | 4/2008 | Lee | ......................... | F21K 9/272 |
| | | | | 362/223 |
| 2012/0199005 A1* | 8/2012 | Koji | ................... | F21V 33/0088 |
| | | | | 96/224 |
| 2013/0236353 A1* | 9/2013 | Blechschmidt | ........... | A61L 9/20 |
| | | | | 422/4 |
| 2014/0050612 A1* | 2/2014 | Kneissl | ............. | G01N 15/1404 |
| | | | | 422/24 |
| 2016/0009570 A1* | 1/2016 | Yu | ........................... | C02F 1/325 |
| | | | | 210/748.1 |
| 2017/0281812 A1* | 10/2017 | Dobrinsky | ............ | B08B 9/0321 |
| 2017/0340760 A1* | 11/2017 | Starkweather | ............ | A61L 2/24 |
| 2019/0167826 A1* | 6/2019 | Winslow | ............... | F21V 15/015 |
| 2019/0201570 A1* | 7/2019 | Dobrinsky | ................ | A23L 3/28 |
| 2019/0310275 A1* | 10/2019 | Ishida | ....................... | C02F 1/32 |

FOREIGN PATENT DOCUMENTS

KR   10-2019-0132737 A   11/2019

* cited by examiner

*Primary Examiner* — Andrew Smyth
(74) *Attorney, Agent, or Firm* — Novick, Kim & Lee, PLLC; Jae Youn Kim

(57) ABSTRACT

Disclosed herein is a light emitting diode (LED) lighting device for sterilizing a surface or a space capable of effectively performing short-distance sterilization or long-distance sterilization. The device includes: a body including an inner transparent tube and an outer transparent tube in a double-tube type, the inner transparent tube forming a vertical ventilation hole and the outer transparent tube being spaced apart from the inner transparent tube at a predetermined distance; a substrate provided in a space formed by the inner transparent tube and the outer transparent tube; and a first light emitting element and a second light emitting element provided on an outer surface of the substrate. The first light emitting element emits visible light having a first wavelength of 405 nm, and the second light emitting element emits short-wavelength visible light having a second wavelength in the range of 400 to 450 nm.

8 Claims, 12 Drawing Sheets

LED LIGHTING DEVICE FOR STERILIZING SURFACE OR SPACE

CROSS REFERENCE TO RELATED APPLICATION

The present application claims priority to Korean Patent Application No. 10-2020-0116840, filed on 9 Nov. 2020, the entire contents of which is incorporated herein for all purposes by this reference.

BACKGROUND

1. Technical Field

The present invention relates to a sterilizing device, and more particularly, to a light emitting diode (LED) lighting device for sterilizing a surface or a space capable of emitting light at different wavelengths to effectively perform short-distance sterilization or long-distance sterilization without causing damage to a human body, thereby maximizing a sterilization effect, and capable of sterilizing bacteria in circulating air to purify the air.

2. Description of the Related Art

Biological etiologies causing diseases in humans, such as bacteria, viruses, fungi, and parasites, always exist around us.

These etiologies can turn into great threats to humans at any time as seen in the pandemic situation caused by the recent new coronavirus.

For this reason, there has been an increasing need to perform sterilization, pasteurization and/or disinfection (hereinafter, collectively referred to as sterilization) around our living spaces more routinely. Accordingly, the demands for various sterilization products that can be used around our living spaces have been increasing.

Sterilization products containing liquid-type antibacterial agents or disinfectants in containers are widely used around our living spaces, not only in general homes but also in offices, restaurants, hospitals, public facilities, public transportations, and the like. These liquid-type products decreases in amount whenever used, and thus, there is a disadvantage in that frequent replacements are required. In addition, the liquid-type products may cause discomfort, such as a sticky feeling, when applied to skin.

As non-contact type sterilizers, optical sterilizers emitting light such as ultraviolet (UV) rays for sterilization are widely used.

Recently, UV emitting diodes (LEDs) emitting ultraviolet rays have been variously developed for use in optical sterilizers.

Among them, UV-C LEDs having a wavelength in the range of 100 to 280 nm are known to have the best sterilization effect.

These ultraviolet sterilizers have a problem in that ultraviolet rays emitted for sterilization are also harmful to human bodies, and thus, additional facilities are required to prevent the emitted light from reaching people, or installation spaces, operation times, and the like are limited.

Meanwhile, among the optical sterilizers, sterilizers using LEDs emitting visible light having a wavelength of 405 nm to perform sterilization are known. The visible light having a wavelength of 405 nm is not only harmless to the human bodies but also capable of destroying bacterial cells based on porphyrin-reactive decomposition for sterilization. However, conventional sterilizers using the LEDs that emit visible light having a wavelength of 405 nm are effective for short-distance sterilization, but inferior in long-distance sterilization.

RELATED ART DOCUMENT

Patent Document (Patent Document 1) KR 10-2019-0132737 A (Published on Nov. 29, 2019)

SUMMARY

An object of the present invention is to provide a light emitting diode (LED) lighting device for sterilizing a surface or a space capable of emitting light at different wavelengths to effectively perform short-distance sterilization or long-distance sterilization without causing damage to a human body, thereby maximizing a sterilization effect, and capable of sterilizing bacteria in circulating air to purify the air.

According to an embodiment of the present invention, an LED lighting device for sterilizing a surface or a space includes: a body including an inner transparent tube and an outer transparent tube in a double-tube type, the inner transparent tube forming a vertical ventilation hole and the outer transparent tube being spaced apart from the inner transparent tube at a predetermined distance; a substrate provided in a space formed by the inner transparent tube and the outer transparent tube; and a first light emitting element and a second light emitting element provided on an outer surface of the substrate. The first light emitting element may emit visible light having a first wavelength of 405 nm, and the second light emitting element may emit short-wavelength visible light having a second wavelength in the range of 400 to 450 nm.

An ultraviolet lamp may be provided on an inner surface of the substrate to face the vertical ventilation hole.

The ultraviolet lamp may emit ultraviolet light having a wavelength in the range of 207 to 222 nm.

The device may further include a stand fixed to a lower surface of the body, the stand having a lower air inlet hole penetrating through a lower surface thereof and a side air inlet hole penetrating through a side surface thereof.

A filter may be provided in the side air inlet hole.

The device may further include a cover spaced apart from an upper end of the body at a predetermined distance.

A display and a speaker may be provided on the cover, the display displaying an on/off state and a contamination level of a surrounding environment.

A circulator may be provided in an air-blow passage formed between the side air inlet hole and the vertical ventilation hole.

The circulator may include: a housing in which a space is formed; an inlet port provided in a shape of a through hole passing through one end portion of the housing to allow external air to be sucked thereinto; an outlet port provided in a shape of a through hole passing through an outer surface of the housing to discharge compressed air; a fan provided in a forward direction of the air-blow passage of the housing; and a motor provided between the housing and the fan.

The motor may include a front brushless direct current (BLDC) motor and a rear BLDC motor.

The front BLDC motor may be axially coupled to a first rotator having a first blade provided on an outer surface thereof with a predetermined inclination angle, and the rear BLDC motor may be axially coupled to a second rotator having a second blade provided on an outer surface thereof with a predetermined inclination angle.

The inclination angle of the first blade and the inclination angle of the second blade may be formed in opposite directions.

The first blade may be a 7-leaf blade and the second blade may be a 5-leaf blade.

DETAILED DESCRIPTION OF THE EMBODIMENTS

Figure 1:
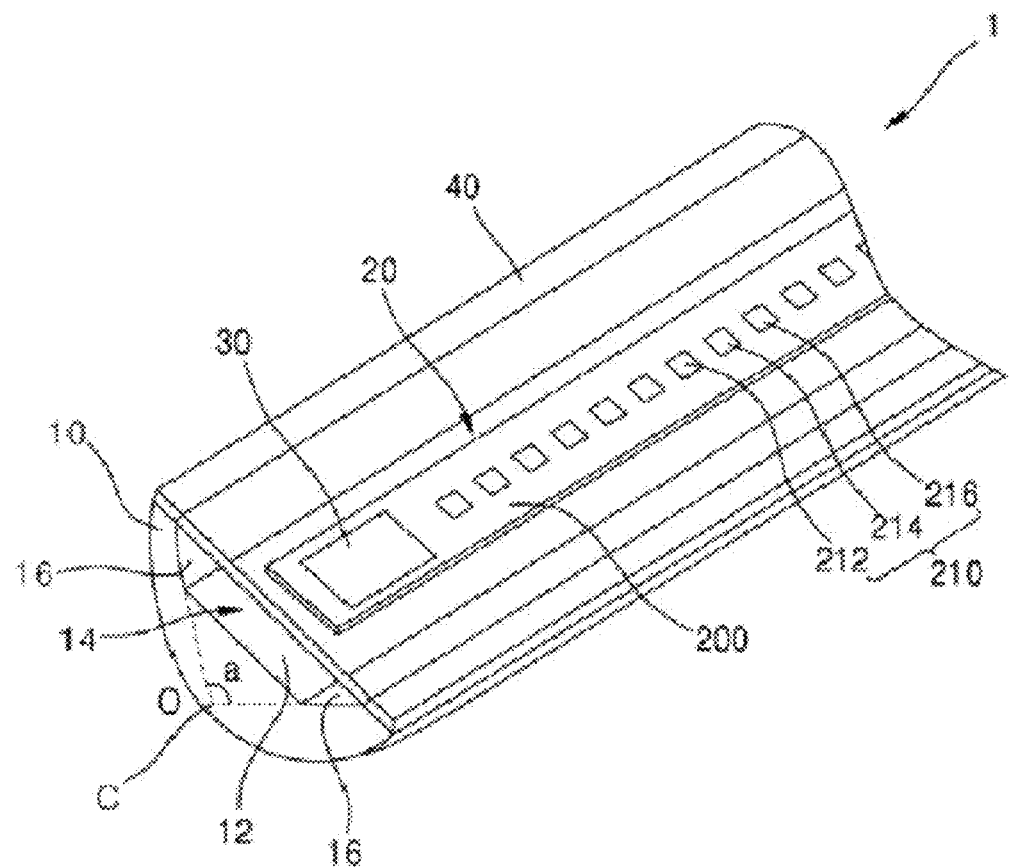
FIG. 1 is a schematic perspective view of a sterilizing device.

Preferred embodiments of the present invention will be described in detail with reference to the accompanying drawings. For reference, a size of a component, a thickness of a line, etc. illustrated in the drawings to which reference is made to describe the present invention may be somewhat exaggerated for convenience of illustration.

Further, terms used to describe the present invention are defined in consideration of functions in the present invention and therefore may be changed depending on an intention, a practice, or the like of a user or an operator. Therefore, the definition of the terminologies should be construed based on the contents throughout the specification.

It should be further understood that the term "include", "have", or the like in the present application is used to denote the existence of the specific features, numbers, steps, operations, components, parts, or combinations thereof stated in the specification, while not precluding the existence or addition of one or more other features, numbers, steps, operations, components, parts, or combinations thereof.

In addition, the present invention is not limited to embodiments which will be described below, but may be implemented in many different forms. The embodiments may be provided so that this disclosure will be thorough and complete, and will fully convey the scope of the invention to those skilled in the art.

Since the present invention may be modified in various ways and take on various forms, particular embodiments will be described in detail in the specification. However, it should be understood that the present invention is not limited to the particular embodiment disclosed herein, but includes all modifications, equivalents, and alternatives included in the spirit and the scope of the present invention. Singular forms used herein are intended to include plural forms unless the context clearly indicates otherwise.

In describing the present invention, the detail description of known functions or components will be omitted in order to clarity the gist of the present invention.

Hereinafter, specific embodiments of the present invention will be described with reference to the drawings.

FIG. 1 is a schematic perspective view of a sterilizing device.

As illustrated, the sterilizing device 1 includes a body 10, a light emitter 20, and a controller 30.

The body 10, which is a base member or a frame member forming the skeleton of the sterilizing device 1, may have various structures and/or shapes for mounting the light emitter 20, which will be described later. For example, as illustrated in FIG. 1, the body 10 is generally formed as a rectangular container member extending to be elongated along an axial direction C.

The body 10 may include a main surface 12, on which the light emitter 20 is mounted, on one side thereof in a direction perpendicular to the axial direction C (hereinafter, referred to as the radial direction). The main surface 12 may be a plane surface following the axial direction C of the body 10.

The body 10 may include a recess 14 formed to be concave inwardly in the radial direction.

Accordingly, when viewed from above one end of the sterilizing device 1 in the axial direction C, at least a part of the body 10 may have a cross section in an approximately "U" or "⊏" shape. The main surface 12 may be a surface formed on an inner side of the recess 14 in the radial direction. The light emitter 20 may be disposed in the recess 14 and mounted on the main surface 12.

A reflective surface 16 may be formed in the recess 14. The reflective surface 16 may extend outwardly in the radial direction from an edge of the main surface 12.

The reflective surface 16 may extend in the axial direction C along the entire length of the main surface 12. The reflective surface 16 may be formed to entirely surround the main surface 12.

The reflective surface 16 may include a pair of reflective surfaces 16 extending from both ends of the main surface 12 that are opposite to each other. The pair of reflective surfaces 16 may extend outwardly in the radial direction from the both opposite ends of the main surface 12 in such a manner as to be oblique at a predetermined angle.

Accordingly, when viewed from above the one end of the sterilizing device 1 in the axial direction C, the pair of reflective surfaces 16 may form a predetermined divergence angle a from an intersection point O where virtual extension lines thereof meet. The divergence angle a may be, for example, 120 degrees.

The main surface 12 and the reflective surfaces 16 may form one continuous curved surface.

For example, when the recess 14 is formed to be concave inwardly in the radial direction of the body 10 in such a manner as to have a curved surface, each of the main surface 12 and the reflective surfaces 16 may constitute some of the curved surface.

In this case, while the surfaces in the recess 14 located on the opposite sides of the main surface 12, on which the light emitter 20 is mounted, are formed as the pair of reflective surfaces 16, the divergence angle formed by the pair of reflective surfaces 16, for example an angle formed by two extension lines connecting the intersection O and respective ends of the pair of reflective surfaces 16 in the radial direction, may be 120 degrees, when viewed from above the one end of the sterilizing device 1 in the axial direction C.

The reflective surface 16 may be formed to include a plurality of divided surfaces (not shown) that are separate from each other. Even in this case, the divergence angle, for example an angle formed by two extension lines connecting the intersection O and respective ends of the outermost ones of the plurality of divided surfaces in the radial direction, may be 120 degrees, when viewed from above the one end of the sterilizing device 1 in the axial direction C.

A light reflective film (not shown) may be formed on the reflective surface 16. The light reflective film may be formed by applying a paste material to the reflective surface 16, the paste material including a resin material having excellent light reflecting properties, such as epoxy, a metal material, such as aluminum or silver, etc.

The light reflective film may be formed on the main surface 12 as well. In this case, the main surface 12 may also function as a reflective surface. When the body 10 itself is formed of a material having excellent light reflecting properties, a separate light reflective film may not be formed on the reflective surface 16 and/or the main surface 12.

The above-described structures and/or shapes of the body 10 are merely exemplary, and the body 10 is not limited to the above-described structures and/or shapes.

For example, the body 10 may be formed in a cubic or spherical shape, and may be formed in a plate or sheet shape.

The body 10 may be formed to have a cross-sectional shape in a various manner, such as a semi-circular shape, a semi-elliptical shape, a circular shape, an elliptical shape, or a polygonal shape (including a triangular shape, a square shape, a hexagonal shape, an octagonal shape, and the like).

It is illustrated in FIG. 1 that the body 10 has a significant thickness, but the thickness of the body 10 is not limited thereto. The body 10 may be manufactured by processing a thin plate material to have a predetermined shape.

The body 10 may be formed of various kinds of materials. The body 10 may be formed of a material including plastic, ceramic, metal, or a combination thereof.

For example, as the base member of the sterilizing device 1, the body 10 may be entirely formed of a thermosetting plastic material, such as epoxy, to have a certain rigidity and insulation.

In addition, the body 10 may be formed of a metal material having good heat dissipation, such as aluminum. In this case, an insulating material may be applied onto a surface of the metal material.

The light emitter 20, which is a light emitting member for emitting sterilizing light, may include a plurality of light emitting elements 210 arranged on a substrate 200.

The substrate 200, which is a member for mounting the plurality of light emitting elements 210 thereon, may be, for example, a rectangular thin board or sheet member extending along the axial direction C, as illustrated in FIG. 1.

The substrate 200 may include a conductive circuit pattern (not shown) formed on an insulating base material and electrically connected to the plurality of light emitting elements 210, and a connection terminal (not shown) connected to the conductive circuit pattern for electrical connection to an external wiring.

The substrate 200 may be electrically connected to an external power supply and/or the controller 30, which will be described later, through the connection terminal. The controller 30 may be mounted on the substrate 200.

As the substrate 200, for example, a single-layer or multi-layer printed circuit board (PCB) or flexible printed circuit board (FPCB) substrate or the like may be used.

The substrate 200 may be disposed on at least a part of the main surface 12 of the body 10. The plurality of light emitting elements 210 may be disposed on the substrate 200. The plurality of light emitting elements 210 may be arranged along a length direction and/or a width direction of the substrate 200. The plurality of light emitting elements 210 arranged on the substrate 200 may be connected to the conductive circuit pattern for electrical connection to the external wiring through the connection terminal.

The plurality of light emitting elements 210, which is a member emitting sterilizing light in the sterilizing device 1 according to an embodiment of the present invention, may include two or more light emitting elements that emit light at different wavelengths from each other.

For example, the plurality of light emitting elements 210 may include a first light emitting element 212 and a second light emitting element 214 that emit light at different wavelengths from each other.

The first light emitting element 212 may emit light having a first wavelength $\lambda 1$. The light of the first wavelength $\lambda 1$ may be visible light having a wavelength of 405 nm.

For general ultraviolet sterilization, a method of destroying bacterial DNAs using ultraviolet C (UV-C) light having a wavelength in the range of 100 to 280 nm is used.

The UV-C light is known to have the most superior sterilization effect, but may be harmful to a human's eyes, skin, or the like. Thus, additional facilities are required to prevent the emitted ultraviolet light from reaching human bodies, or installation spaces, operation times, and the like should be limited.

In this regard, it has been proven by research results that the visible light having a wavelength of 405 nm is not only capable of effectively destroying bacterial, viral, and microbial cells and the like based on porphyrin-reactive decomposition, but also harmless to the human body, because it is visible light.

The visible light having a wavelength of 405 nm is superior in the sterilizing effect against various microbes, bacteria, viruses, and the like, such as *Salmonella*, Pneumococcus, Coronavirus, *Escherichia coli*, *Pseudomonas aeruginosa*, and *Staphylococcus aureus*. The visible light having a wavelength of 405 nm is capable of effective sterilization, while not causing the damage to the human body, without the problems as caused by the UV-C light.

However, a large amount of energy is required to cause the porphyrin-reactive decomposition using the visible light having a wavelength of 405 nm. For this reason, a conventional sterilizing device using visible light having a wavelength of 405 nm has a problem in that an active sterilization distance is considerably short, and thus, it is only possible to perform short-distance sterilization and it is difficult to perform long-distance sterilization.

For example, the conventional sterilizing device has a superior effect in short-distance sterilization within about 30 to 50 cm, but the sterilization effect significantly decreases at a long distance of 1 m or more.

As a result of intensively researching and reviewing a method capable of exhibiting an excellent sterilization effect even at a long distance of 1 m or more while using the visible light having a wavelength of 405 nm, the inventors of the present invention have arrived at a device for forming mixed light by mixing visible light having a wavelength of 405 nm and short-wavelength visible light having a wavelength that is close thereto.

That is, in the sterilizing device 1 according to an embodiment of the present invention, the second light emitting element 214 may emit light having a second wavelength $\lambda 2$. The light of the second wavelength $\lambda 2$ may be short-wavelength visible light having a different wavelength from the light of the first wavelength $\lambda 1$.

Here, the short-wavelength visible light may be visible light having a wavelength in the range of 400 to 450 nm. The short-wavelength visible light may be mixed with visible light having a wavelength of 405 nm, which is the light of the first wavelength $\lambda 1$, to form mixed light.

When compared to the visible light having a single wavelength of 405 nm, the mixed light formed by mixing short-wavelength visible light with visible light having a wavelength of 405 nm, which is the light of the first wavelength $\lambda 1$, is capable of effectively sterilizing objects that are located even at a long distance of 1 m or more.

This may be because the short-wavelength visible light having a wavelength in the range of 400 to 450 nm provides energy required for sterilization at a long distance of 1 m or more using the visible light having a wavelength of 405 nm.

The short-wavelength visible light in the range of 400 to 450 nm is capable of sterilization against other types of bacteria and the like that are difficult for the visible light having a wavelength of 405 nm to perform sterilization against. Thus, the sterilization effect can be further improved by forming the mixed light of the short-wavelength visible light and the visible light having a wavelength of 405 nm.

The light of the second wavelength $\lambda 2$ emitted by the second light emitting element 214 may be white light having a color temperature of 9,000 K or more. When the visible light having a wavelength of 405 nm is mixed with the white light having a color temperature of 9,000 K or more to form mixed light, sterilization may be effectively performed at a long distance of not only 1 m or more but also more than 2 m.

On the other hand, when the visible light having a wavelength of 405 nm is mixed with white light having a color temperature of less than 9,000 K, it is not possible to obtain a sufficient long-distance sterilization effect.

Both the visible light having a wavelength of 405 nm and the short-wavelength visible light are harmless to the human body. Thus, the mixed light of the light of the first wavelength $\lambda 1$ and the light of the second wavelength $\lambda 2$ may also be used as illumination light in everyday living spaces where people live.

Figure 2:
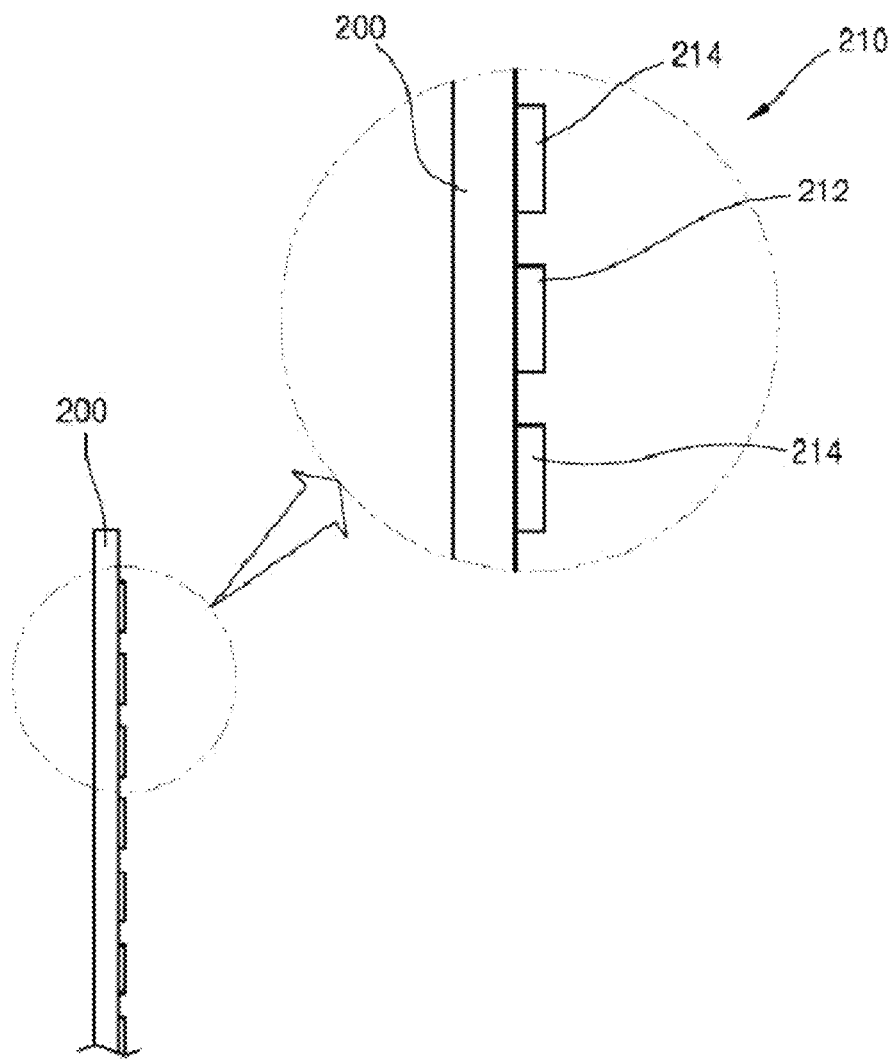
FIG. 2 is an arrangement diagram of light emitting elements.

FIG. 2 is a diagram illustrating an example in which the light emitting elements 210 are arranged.

Referring to FIG. 2, the first light emitting element 212 and the second light emitting element 214 may be arranged adjacent to each other.

For example, as illustrated in FIG. 2, the second light emitting elements 214 may be arranged on both sides of the first light emitting element 212 along the length direction of the substrate 200. The first light emitting element 212 and the second light emitting elements 214 may be arranged at regular intervals.

For example, the first and second light emitting elements 212 and 214 may be arranged at intervals of about 20 mm.

Accordingly, it is possible to form the mixed light in which the light of the first wavelength $\lambda 1$ emitted from the first light emitting element 212 and the light of the second wavelength $\lambda 2$ emitted from the second light emitting element 214 are mixed.

In the above-described mixed light, amounts of the light of the first wavelength $\lambda 1$ and the light of the second wavelength $\lambda 2$ or a mixing ratio thereof may be adjusted variously, in consideration of a contamination level, a target to be sterilized, etc, when used.

For example, when the contamination level is high due to bacteria such as *Staphylococcus*, a proportion of the visible light having a wavelength of 405 nm, which is the light of the first wavelength $\lambda 1$, may be increased.

In addition, the mixing ratio of the light of the first wavelength $\lambda 1$ and the light of the second wavelength $\lambda 2$ may be adjusted in consideration of whether the light functions as illumination light or as sterilization light depending on whether or not there is a person or a distance from a human body.

For example, when there is a person within 1 m, the light may preferentially function as illumination light by adjusting the mixing ratio such that the mixed light includes 20% of the visible light having a wavelength of 405 nm and 80% of the white light having a wavelength in the range of 400 to 450 nm.

Thereafter, when the person moves away beyond 1 m, the proportion of the visible light having a wavelength of 405 nm is gradually increased, and when the person moves away beyond 2 m, the mixing ratio may be adjusted such that the mixed light includes 50% of the visible light having a wavelength of 405 nm and 50% of the white light having a wavelength in the range of 400 to 450 nm.

When there is no person, the light may preferentially function as sterilization light, and the mixing ratio may be adjusted such that the mixed light includes 80% of the visible light having a wavelength of 405 nm and 20% of the white light having a wavelength in the range of 400 to 450 nm. These mixing ratios are exemplary, and the mixing ratio can be appropriately set in consideration of several variables in an actual environment where the sterilizing device 1 is installed.

The mixing ratio of the light of the first wavelength $\lambda 1$ and the light of the second wavelength $\lambda 2$ may be adjusted by the controller 30, which will be described later.

Figure 3:
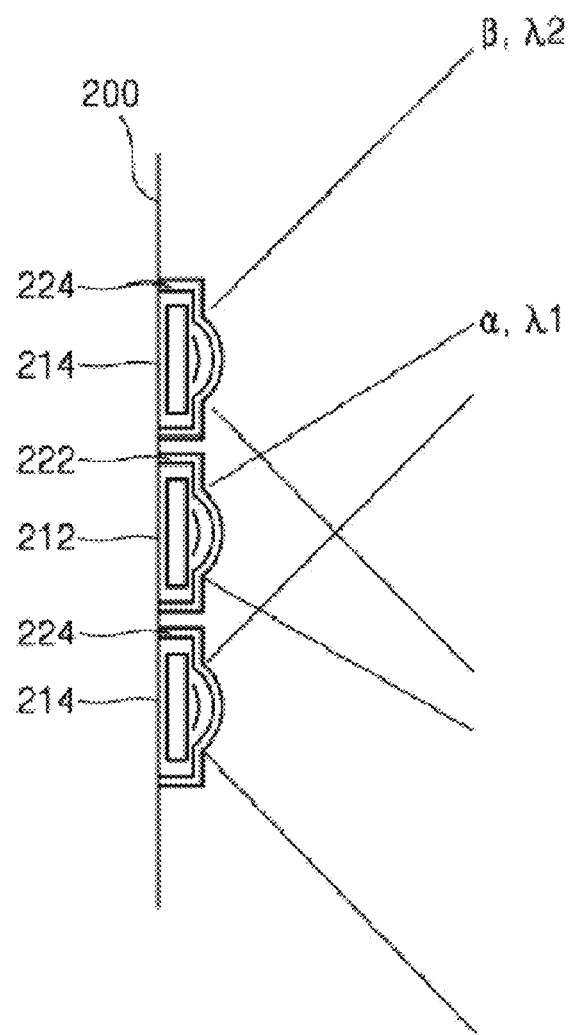
FIG. 3 is a state diagram illustrating emission angles of light emitted from the light emitting elements.

FIG. 3 is a diagram illustrating emission angles of light emitted from the light emitting elements 210.

The first light emitting element 212 may emit the light of the first wavelength $\lambda 1$ at a first angle $\alpha$. The first angle $\alpha$ may be an acute angle greater than 0 degrees and smaller than 90 degrees.

For example, the first angle $\alpha$ may be an acute angle of about 60 degrees. By emitting the visible light having a wavelength of 405 nm, which is the light of the first wavelength $\lambda 1$, at the acute angle, the optical energy of the light of the first wavelength $\lambda 1$ can be focused such that the light not only reaches a longer distance but also effectively performs sterilization at a longer distance.

In order to adjust the emission angle of the light of the first wavelength $\lambda 1$ to the acute angle, a first optical element 222 may be disposed on an optical path of the first light emitting element 212.

As the first optical element 222, any one of various optical means capable of focusing the light of the first wavelength $\lambda 1$ from the first light emitting element 212 to be emitted at an acute angle may be employed.

For example, the first optical element 222 may be a convex lens focusing diffused light.

Of course, the first optical element 222 is not limited only to the convex lens. For example, a transparent silicone resin sealing the first light emitting element 212 may be formed in the same shape as the convex lens, or a diffraction pattern or the like may be formed on a cover 40, which will be described later, to focus the light of the first wavelength $\lambda 1$ such that the light is emitted at an acute angle.

Meanwhile, the second light emitting element 214 may emit the light of the second wavelength $\lambda 2$ at a second angle $\beta$. The second angle $\beta$ may be an obtuse angle greater than 90 degrees and smaller than 180 degrees.

For example, the second angle $\beta$ may be an obtuse angle of about 120 degrees. By emitting the light of the second wavelength $\lambda 2$ from the second light emitting element 214, which is disposed adjacent to the first light emitting element 212, at the obtuse angle, the light of the second wavelength $\lambda 2$ can be diffused further widely into the optical path of the light of the first wavelength $\lambda 1$.

Accordingly, it is possible to more uniformly mix the light of the second wavelength $\lambda 2$ with the light of the first wavelength $\lambda 1$, and it is possible to provide sufficient optical energy required for the light of the first wavelength $\lambda 1$ to have the sterilization effect at a longer distance.

In order to adjust the emission angle of the light of the second wavelength $\lambda 2[N1]$ to the obtuse angle of about 120 degrees, a second optical element 224 similar to the first optical element 222 may also be disposed on an optical path of the second light emitting element 214.

When the light of the second wavelength $\lambda 2$ itself is diffused light emitted from the second light emitting element 214 at an emission angle in the above-described range, the second optical element 224 may be omitted.

The plurality of light emitting elements 210 may further include a third light emitting element 216.

The third light emitting element 216 may emit light having a third wavelength $\lambda 3$ that is different from the first wavelength $\lambda 1$ and the second wavelength $\lambda 2$.

The light of the third wavelength $\lambda 3$ may be ultraviolet light. For example, the light of the third wavelength $\lambda 3$ may be far short-wavelength ultraviolet (far-UVC) light having a wavelength in the range of 207 to 222 nm.

Generally used UV-C light having a wavelength in the range of 100 to 280 nm may cause damage such as injury to eyes if exposed directly to the human body.

In contrast, the far-UVC light having a wavelength in the range of 207 to 222 nm is ultraviolet light but is not capable of penetrating into the human body, in particular erythema. Thus, the far-UVC light is capable of rapid sterilization, without causing injury to the eyes, even when exposed directly to the human body.

As an example of the third light emitting element 216, a light emitting element emitting light having a wavelength in the range of 207 to 222 nm may be used. Even when a UV-C light emitting element having a wavelength in the range of 100 to 280 nm is used, a filter only allowing light having a wavelength in the range of 207 to 222 to pass therethrough may be installed on an optical path of the UV-C light emitting element, thereby generating the far-UVC light having a wavelength in the range of 207 to 222 nm from the third light emitting element 216.

Accordingly, rapid sterilization can be performed without causing injury to the eyes or the like. Therefore, in a case where there is no person or there is no concern that the sterilizing light may reach eyes, it is possible to efficiently perform sterilization by means of the far-UVC light emitted from the third light emitting element 216.

As the plurality of light emitting elements 210, light emitting diodes (LEDs) may be used. Of course, the light emitting elements 210 are not limited only to the LEDs, and another type of known light emitting means such as fluorescent lamps may be used as long as the purpose and/or effect is equivalent.

The light emitter 20 having the plurality of light emitting elements 210 arranged on the substrate 200 according to an embodiment of the present invention may be independently provided as a light emitting module for sterilization and/or illumination.

In addition, the light emitter 20 may be provided together with the controller 30, which will be described later, in the form of a module.

Figure 4:
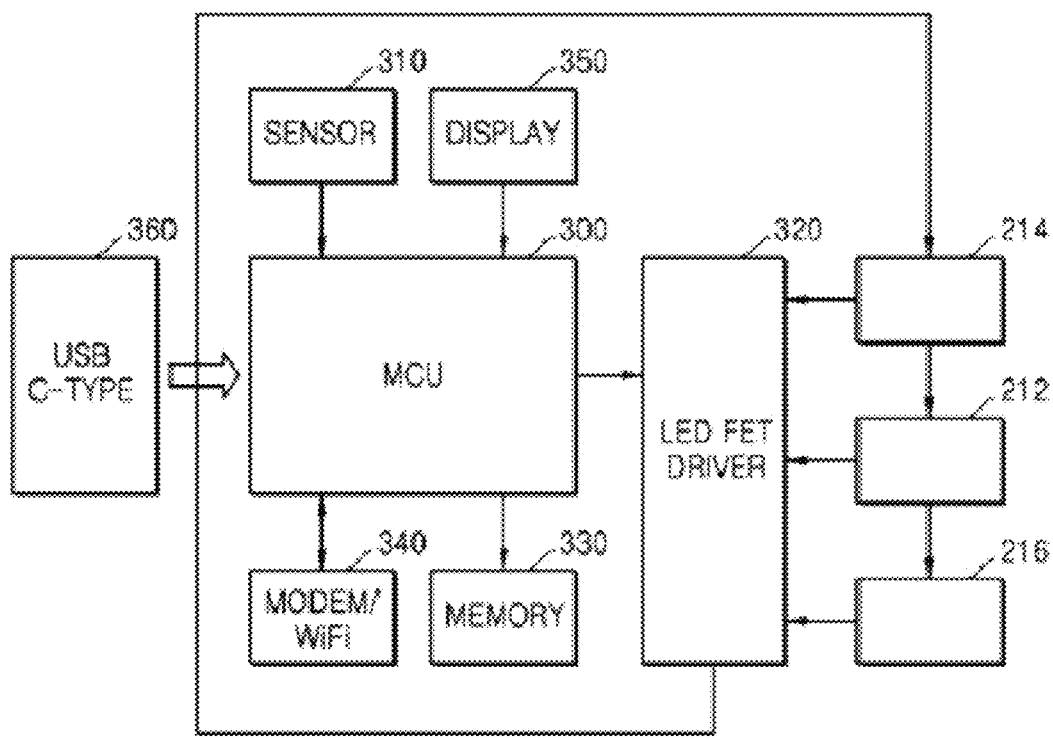
FIG. 4 is a schematic block diagram of a controller.

FIG. 4 is a block diagram illustrating a schematic configuration of the controller 30.

Referring to FIG. 4, the controller 30 may include a processor 300, a sensor 310, and a light emitting element driver 320. The controller 30 may further include a memory 330, a communicator 340, a display 350, and an input/output terminal 360.

The processor 300, which is a part processing data or signals to control an overall operation, may include, for example, a data processing unit such as a micro controller unit (MCU).

The sensor 310 may be connected to various types of externally-installed sensors to transmit signals that are input from the sensors.

As the sensors connected to the controller 30, various types of sensors may be appropriately included according to the need, for example, a contamination level sensor indicating a contamination level of a surrounding environment, a bacteria sensor indicating whether or not there is bacteria or a concentration of bacteria, a motion detection sensor indicating whether or not there is a person or a moving object, and a distance sensor indicating a distance from the person or the moving object.

The light emitting element driver 320, which is a part controlling an operation of the plurality of light emitting elements 210, may include, for example, a field effect transistor (PET) driver for driving LEDs.

The light emitting element driver 320 may control an on/off state, a duty cycle, and the like of each of the light emitting elements 212, 214 and 216.

The memory 330, which is a part storing data, programs, and the like required for driving the sterilizing device 1, may include, for example, a memory such as a random-access memory (RAM) or an electrically erasable and programmable read only memory (EEPROM).

The communicator 340, which is a part accessing to a network (e.g. a local area network (LAN), a wide area network (WAN), or the Internet) in a wired or wireless manner to transmit and receive data or signals to/from the outside, may include, for example, a wired or wireless communication means such as a modem or a wireless fidelit (WIFI) module.

The display 350, which is a part for externally displaying a driving state of the sterilizing device 1, may include, for example, an audio/video unit for displaying audiovisual information indicating the driving state of the sterilizing device 1 through a display means such as a light emitting element, a speaker, or a display panel provided on the body 10 or the like.

The input/output terminal 360, which is a terminal for connection to an external wiring or device, may include a connection terminal for connection to a cable or a terminal for supplying power and/or transmitting data or signals or the like.

A signal or the like that is input by a user through an operator (e.g. an operation panel including an on/off switch, a mode change switch, and the like) provided on the body 10 or the like may also be input to the controller 30 through the input/output terminal 360.

The user may select a driving mode of the sterilizing device 1, when used, through the operator provided on the body 10 or the like.

The selected driving mode may be input to the controller 30 through the input/output terminal 360. For example, an automatic mode for automatically adjusting a driving mode according to a surrounding environment detected by the sensor 310 may be selected.

The sensor 310 may include a distance sensor detecting a distance from a person or a moving object.

The controller 30 may adjust a duty cycle for each of the light emitting element 212, 214 and 216 according to the distance from the person or the moving object detected by the sensor 310. The control of the duty cycle may be performed through, for example, pulse width modulation (PWM) as illustrated in FIGS. 5A-5E.

FIGS. 5A-5E are a diagram illustrating an example in which the duty cycle of the light emitting element 210 is controlled by the controller 30 through PWM. In FIGS. 5A-5E, a transverse axis represents a clock period, and a longitudinal axis represents a voltage.

The controller 30 may control an intensity of emitted light to be increased or decreased by instantaneously emitting a high current using a peak value of a frequency using a variable frequency of 60 Hz to 1 MHz.

Figure 5:
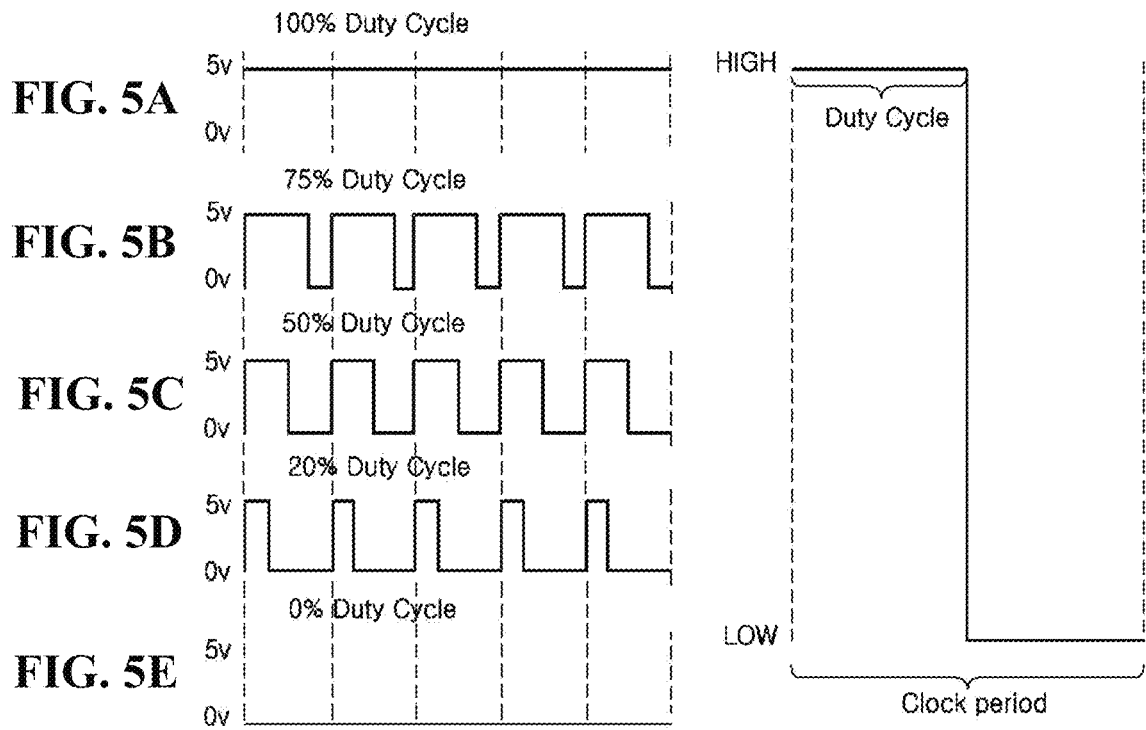
FIGS. 5A-5E are a state diagram illustrating an example in which a duty cycle of the light emitting element is controlled by the controller through pulse width modulation (PWM).

Referring to FIGS. 4 and 5A-5E, for example, when no person or moving object is detected by the sensor 310, the controller 30 may control the light emitting element driver 320 to drive the first and second light emitting elements 212 and 214 at a duty cycle of 100% as illustrated in FIG. 5A.

Accordingly, the mixed light of the visible light having a wavelength of 405 nm, which is the light of the first wavelength of λ1, and the short-wavelength visible light having a wavelength in the range of 400 to 450 nm, which is the light of the second wavelength λ2, can be emitted from the sterilizing device 1.

Thus, it is possible to effectively perform sterilization not only at a short distance of less than 1 m but also at a long distance of 1 m or more.

Thereafter, when a person or a moving object is detected by the sensor 310, the duty cycle of the first light emitting element 212 emitting the light of the first wavelength λ1 may be appropriately reduced, in a state where the duty cycle of the second light emitting element 214 emitting the light of the second wavelength λ2 is maintained at 100%.

For example, when the person or the moving object is located at a long distance of 2 m or more, the duty cycle of the first light emitting element 212 may be reduced to 75% as illustrated in FIG. 5B. When the person or the moving object is located at a long distance of between 1 and 2 m, the duty cycle of the first light emitting element 212 may be reduced to 50% as illustrated in FIG. 5C. When the person or the moving object is located at a short distance of less than 1 mm, the duty cycle of the first light emitting element 212 may be reduced to 25% as illustrated in FIG. 5D.

Thus, it is possible to minimize a function as sterilization light and increase a function as illumination light.

When the person approaches at a distance of less than 1 m, the first light emitting element 212 is set to be an off-state at a duty cycle of 0% as illustrated in FIG. 5E, thereby making it possible to perform sterilization in a further harmless manner with respect to the human body.

In either case, the light of the first wavelength λ1 and the light of the second wavelength λ2 are visible light that is harmless to the human body. Thus, it is possible to effectively perform sterilization even at a long distance of 1 m or more without causing injury to the human body.

In addition, when the short-distance sterilization alone is fine enough, only the first light emitting element 212 emitting the visible light having a wavelength of 405 nm may be controlled at a duty cycle of 100%, and the other light emitting elements may be set to be an off-state.

In addition, when there is no person or moving object, only the third light emitting element 216 emitting far short-wavelength ultraviolet light may be set to have a duty cycle of 100%, and the other light emitting elements may be set to be an off-state.

Accordingly, it is possible to efficiently sterilize a sterilization space while minimizing energy consumed by operating the light emitting elements.

Referring back to FIG. 1, the sterilizing device 1 may further include a cover 40.

The cover 40, which is a member protecting the light emitter 20 installed in the body 10, may be formed of a material having excellent light transmittance, such as a transparent resin or glass.

The cover 40 may be formed in such a size as to at least cover the whole of the light emitter 20.

For example, as illustrated in FIG. 1, the cover 40 may entirely cover the recess 14 formed in the body 10.

The cover 40 may be detachably coupled to the body 10 in a screw-fastened manner, in a fitted manner, or the like.

For example, the cover 40 has a plurality of claws (not shown) protruding toward the body 10 at an edge thereof along the perimeter thereof, and the body 10 has a plurality of recesses formed at positions corresponding to the plurality of claws, so that the cover 40 may be coupled to the body 10 by fitting each of the claws into a respective one of the recesses corresponding thereto.

In addition, the cover 40 may be separated from the body 10 by releasing each of the claws from the respective one of the recesses.

The cover 40 may include a light diffusion layer for promoting diffusion of light emitted from the plurality of light emitting elements 210.

For example, the cover 40 may be entirely formed as a light diffusion layer by mixing a powder-type material having excellent light reflectance, such as epoxy, aluminum or silver, with the transparent resin, which is used as a material of the cover 40.

In addition, the light diffusion layer may be formed by forming a light diffusion pattern, such as a diffraction pattern or a concave lens pattern, on the cover 40.

In this case, a light focusing pattern (e.g. a fly-eye lens pattern) for focusing the light of the first wavelength λ1 emitted from the first light emitting element 212 may be formed on an area corresponding to the first light emitting element 212 among the plurality of light emitting elements 210, thereby adjusting the emission angle of the light of the first wavelength λ1 to an acute angle.

The sterilizing device 1 according to an embodiment of the present invention configured as described above may be applied in an appropriate form in various environments where the sterilization is needed.

For example, the sterilizing device 1 according to the embodiment of the present invention may be applied to or replaced for an existing lighting device installed on a ceiling or a wall in a general home.

In addition, the sterilizing device 1 according to the embodiment of the present invention may be manufactured in a stand type and installed in a relatively large space, such as an office, a hospital, a school, or a public institution, or manufactured in a hand-held type and applied to sterilize bedclothes, the inside of a vehicle, or the like.

In addition, the sterilizing device 1 according to the embodiment of the present invention may be installed in a vehicle while being applied in such a manner as to simultaneously sterilize a passenger compartment of the vehicle, an air-conditioner filter, etc.

Hereinafter, some examples where the sterilizing device 1 according to an embodiment of the present invention are applied will be described in more detail.

Some application examples to be described below are merely exemplary, and the sterilizing device 1 according to an embodiment of the present invention is not limited only to the application examples to be described below.

In addition, in the following description, the same reference numerals will be used to describe components that are identical, similar or corresponding to those of the above-described sterilizing device 1, and repeated detailed description thereof will be omitted.

Figure 6:
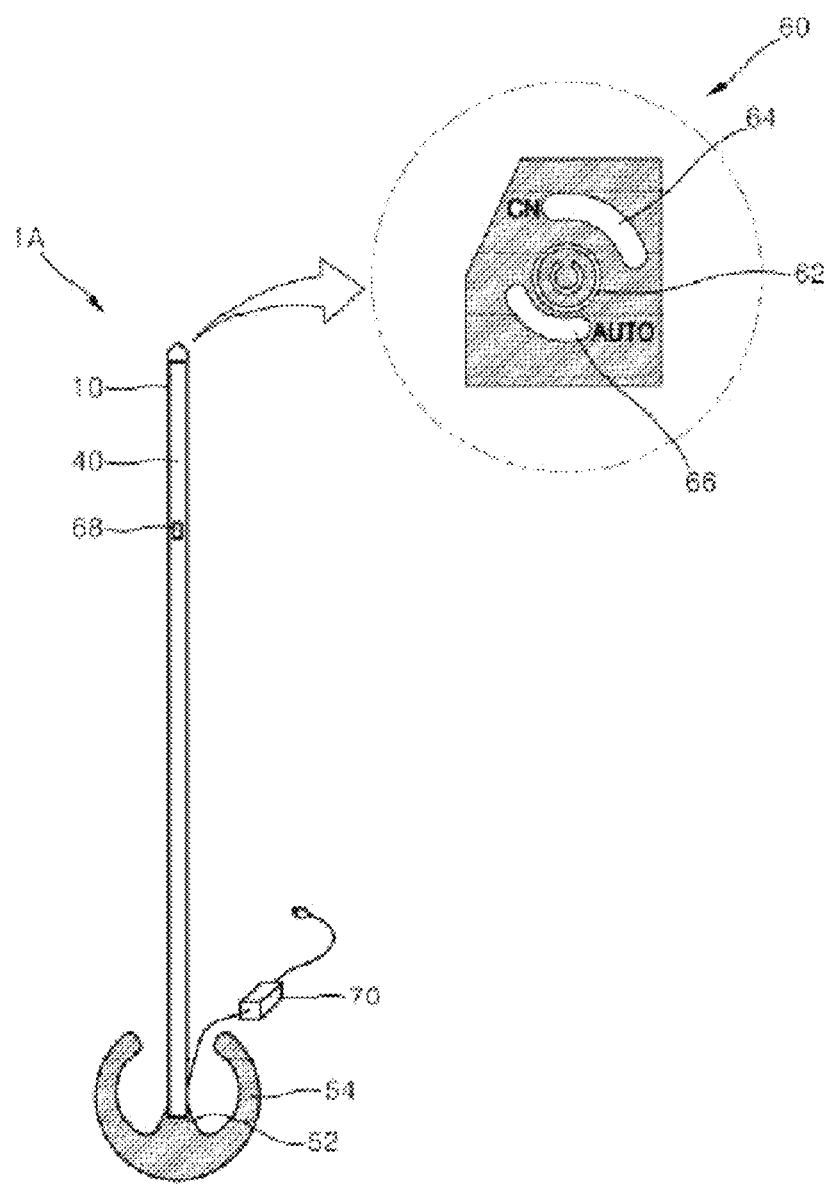
FIG. 6 is a schematic diagram of a stand-type sterilizing device according to an embodiment of the present invention.

FIG. 6 is a diagram schematically illustrating a stand-type sterilizing device 1A according to an embodiment of the present invention.

Referring to FIG. 6, the stand-type sterilizing device 1A may include some or all of the configuration of the above-described sterilizing device 1.

That is, the stand-type sterilizing device 1A may include the body 10, the light emitter 20, and the controller 30 described above. In addition, the stand-type sterilizing device 1A may further include the cover 40 described above.

Here, in the sterilizing device 1 illustrated in FIG. 1, the body 10 has a cross section in an approximately "U" or "⊏" shape when viewed from above one end of the sterilizing device 1 in the axial direction C, and one light emitter 20 is mounted on the main surface 12 of the body 10 in the recess 14.

In contrast, in the stand-type sterilizing device 1A illustrated in FIG. 6, the body 10 may have a cross section in an approximately triangular shape when viewed from above one end of the sterilizing device 1A in the axial direction C, and the triangular body 10 has three sides, each including the recess 14 and the main surface 12, with the light emitters 20 mounted on the respective main surfaces 12.

That is, the stand-type sterilizing device 1A may include three light emitters 20 that are mounted on three main surfaces 12 formed along the perimeter of the body 10 in the axial direction C, each being formed at a position of 120 degrees.

Accordingly, when viewed in a plan view, each of the light emitters 20 may irradiate sterilizing light with respect to a respective region corresponding to a range of 120 degrees.

Thus, the stand-type sterilizing device 1A is capable of evenly sterilizing a space where the stand-type sterilizing device 1A is installed by irradiating the sterilizing light in all directions of 360 degrees in the sterilization space.

Of course, the stand-type sterilizing device 1A is not limited only to such a structure and/or shape. For example, the body 10 may be formed in a plate shape, and two light emitters 20 may be arranged on two main surfaces 12 (e.g. front and rear surfaces) located on opposite sides of the body 10.

In addition, the body 10 may be formed in an approximately cylindrical shape, and a plurality of (e.g. three or more) light emitters 20 may be arranged on an outer circumferential surface of the cylindrical body 10 along a circumferential direction.

Even when one light emitter 20 is mounted on one main surface 12, the light emitter 20 may be configured to emit sterilizing light in all directions of 360 degrees by installing a driving member, such as a motor, in the body 10 so that the body 10 may be rotated in the circumferential direction.

The stand-type sterilizing device 1A may further include a support 50, an operator 60, and an adapter 70.

The support 50, which is a part for installing the sterilizing device 1A upright on a floor in the installation space, may have various structures and/or shapes in which the body 10 is prevented from easily tilting or falling down.

For example, as illustrated in FIG. 6, the support 50 may include a fixer 52 having an approximately container shape for installing the body 10 to be fixed in an upright state, and arc-shaped legs 54 extending from both width-direction ends of the fixer 52 in opposite directions along a horizontal direction.

It is illustrated in FIG. 6 that the body 10 is supported by the pair of legs 54 in the arc shape, but the support 50 is not limited thereto.

Figure 7:
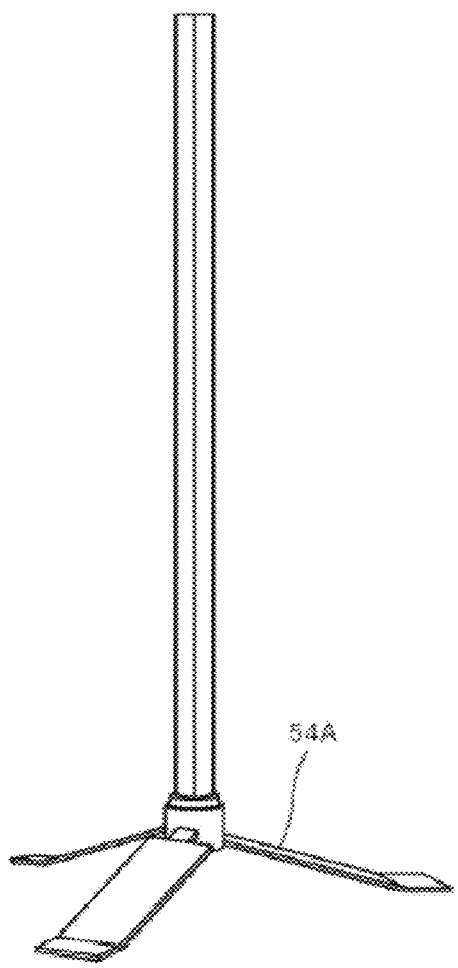
FIG. 7 is a perspective view of a modified example of the stand-type sterilizing device.

For example, as illustrated in FIG. 7, the support 50 may include three foldable legs 54A formed in a paddle shape at a width-direction edge of the fixer 52.

The three foldable legs 54A may be unfolded when installed in such a manner as to each extend downwardly in an oblique way from a position corresponding to 120 degrees in the circumferential direction of the fixer 52 so that the fixer 52 (and the body 10 installed therein) is stably supported at three points in a state where the fixer 52 is slightly spaced apart from the floor of the installation space, and may be compactly stored under the fixer 52 when folded.

In addition, the legs 54 and 54A may include one or more driving wheels (not shown) contacting the floor of the installation space on the bottom thereof.

Accordingly, the stand-type sterilizing device 1A can be easily moved along the floor of the installation space, thereby conveniently installing the sterilizing device 1A at a required position.

The operator 60 may include various switches, display means, and the like for the user to operate the sterilizing device 1A.

For example, the operator 60 may include a power switch 62, an ON LED 64, an AUTO LED 66, and the like. When the user first presses the power switch 62, the sterilizing device 1A may be switched into an a power-on mode, and accordingly, the ON LED 64 may be lighted and sterilization may be initiated by means of sterilizing light.

Thereafter, when the user presses the power switch 62 again, the sterilizing device 1A may be switched into an automatic mode, and accordingly, the AUTO LED 66 may be lighted, and the automatic mode may be executed.

As described above, in the automatic mode, a motion detection sensor 68 or the like is operated to detect the movement of a person or a moving object, so that the sterilizing light may be appropriately adjusted.

Various types of sensors including the motion detection sensor 68 may be installed in the body 10 and/or the support 50.

Thereafter, when the user presses the power switch 62 once again, the sterilizing device 1A may be switched into an power-off mode, and the LED lamp may be off. In addition, the operator 60 may further include a display panel displaying an operating state of the stand-type sterilizing device 1A, surrounding environment information, etc., another operation switch, or the like.

The adapter 70 is a part for supplying power required for the sterilizing device 1A. For example, the adapter 70 may supply a direct current (DC) power of 5V/5 A to the sterilizing device 1A while being connected to an external power supply.

In a case where a battery is mounted in the stand-type sterilizing device 1A itself, the adapter 7 may be excluded.

The stand-type sterilizing device 1A according to an embodiment of the present invention configured as described above is capable of providing an effect equivalent to that of the above-described sterilizing device 1.

In addition, the user may grip the body 10 or a gripping handle formed on the body 10 when moving the stand-type sterilizing device 1A, thereby easily installing the sterilizing device 1A at a position where sterilization is needed.

Accordingly, it is possible to perform more effective sterilization in comparison with a fixed-type sterilizing device fixed to a ceiling or a wall.

Furthermore, since the stand-type sterilizing device 1A can be installed at the center portion on the floor of the installation space, it is possible to preferentially and quickly sterilize a lower area in the installation space affecting the human body by irradiating the sterilizing light with respect to an area corresponding to a height of a person.

In addition, since the sterilizing light can be irradiated in all directions of 360 degrees, it is possible to uniformly and thoroughly sterilize the installation space at all positions.

Figure 8:
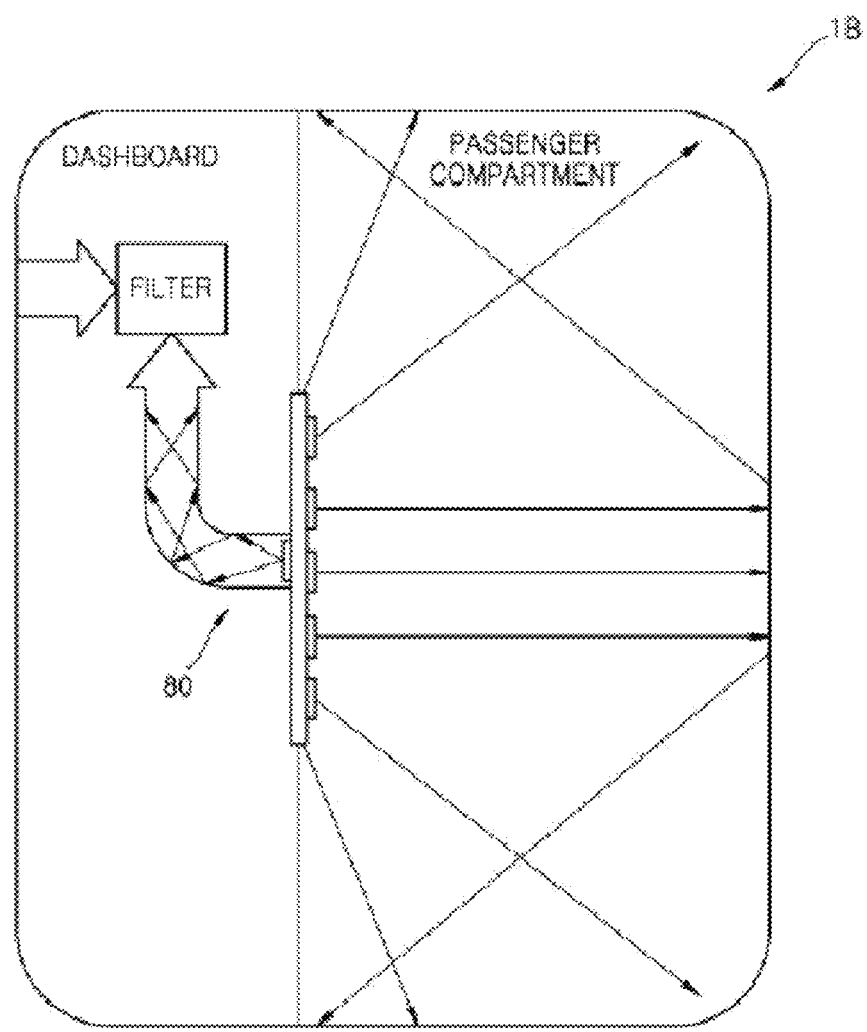
FIG. 8 is a schematic diagram of an in-vehicle sterilizing device according to an embodiment of the present invention.

FIG. 8 is a diagram schematically illustrating an in-vehicle sterilizing device 1B according to an embodiment of the present invention.

Referring to FIG. 8, the in-vehicle sterilizing device 1B may include some or all of the configuration of the above-described sterilizing device 1, like the stand-type sterilizing device 1A.

The vehicle sterilization device 1B may be included in or replaced for a lighting device in a passenger compartment of a vehicle.

For example, the in-vehicle sterilizing device 1B may be installed on a ceiling of the vehicle in a screw-fastened manner or in a bonded manner, or may be attached onto a dashboard by a holder or the like. In addition, the in-vehicle sterilizing device 1B may further include a partial sterilizer 80.

The partial sterilizer 80, which is a part for sterilizing and disinfecting an air-conditioner filter or the like of the vehicle, may be formed in various structures and/or shapes.

For example, a light emitting element 210 for partial sterilization may be separately mounted on one side (e.g. a rear side) of the substrate 200 of the light emitter 20, and sterilizing light emitted therefrom may be guided by a light guide member, such as an optical fiber, toward an area where the air-conditioner filter or the like is installed.

In the area where the air-conditioner filter or the like, illumination light is not needed and there is no risk that the sterilizing light may reach the human body, and thus, only the first light emitting element 212 and/or the third light emitting element 216 may be installed as the light emitting element 210 for sterilizing the filter.

In addition, mixed light formed by the first and second light emitting elements 212 and 214 may be used as sterilizing light for sterilizing the filter.

The in-vehicle sterilizing device 1B according to an embodiment of the present invention configured as described above is capable of providing an effect equivalent to that of the above-described sterilizing device 1.

In addition, since the in-vehicle sterilizing device 1B is attached onto the ceiling of the vehicle or the dashboard to illuminate the passenger compartment of the vehicle, it is possible to uniformly and thoroughly sterilize the passenger compartment of the vehicle at all positions by merely turning on the sterilizing device 1B, thereby sterilizing the passenger compartment of the vehicle in a more simple and effective way, in comparison with a conventional steam-sterilization method or the like.

In addition, the partial sterilizer 80 makes it easy to sterilize and disinfect even an pollutant that is located in the vehicle but is not easy for a human hand to reach, such as the air-conditioner filter.

Figure 9:
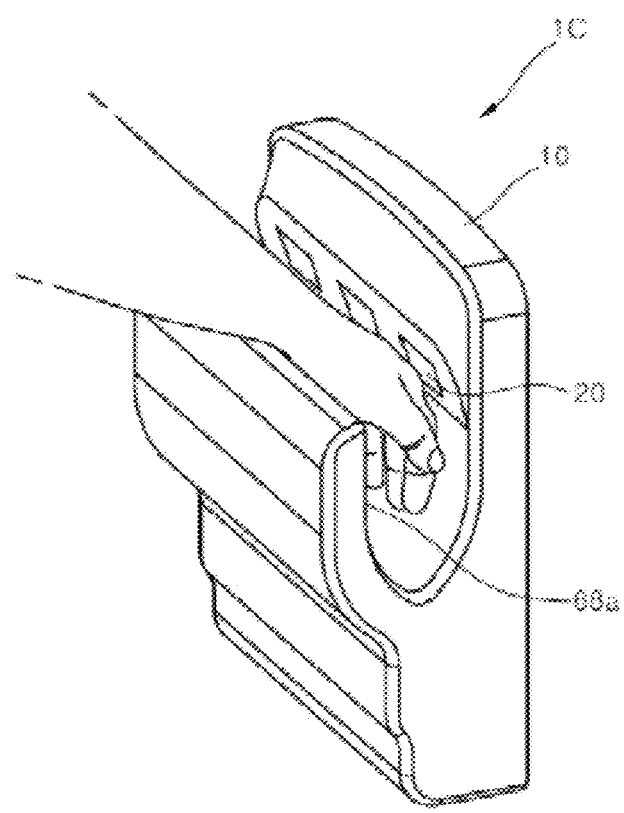
FIG. 9 is a schematic diagram of a hand-disinfection sterilizing device according to an embodiment of the present invention.

FIG. 9 is a diagram schematically illustrating a hand-disinfection sterilizing device 1C according to an embodiment of the present invention.

Referring to FIG. 9, the hand-disinfection sterilizing device 1C may include some or all of the configuration of the above-described sterilizing device 1, like the stand-type sterilizing device 1A.

The hand-disinfection sterilizing device 1C may be included in or replaced for a lighting device or a hand dryer installed in a toilet, an elevator, or the like.

For example, the hand-disinfection sterilizing device 1C may be installed in an existing lighting device or hand dryer installed in a toilet, an elevator, or the like, or may be independently installed on a ceiling or a wall of a toilet, an elevator, or the like in a screw-fastened manner or in a bonded manner.

The hand-disinfection sterilizing device 1C may operate in conjunction with a hand detection sensor 68a detecting that a user's hand has approached.

For example, the hand-disinfection sterilizing device 1C may normally be operated in the above-described automatic mode to perform appropriate sterilization while detecting the movement of a person or a moving object.

When the user tries to dry his/her hands by putting the hands into the hand dryer installed in the toilet, the hand detection sensor 68a may detect that the user's hands have approached, such that air is blown from the hand dryer, and at the same time, sterilizing light is emitted from the hand-disinfection sterilizing device 1C to execute a hand disinfection mode.

The hand-disinfection sterilizing device 1C according to an embodiment of the present invention configured as described above is capable of providing an effect equivalent to that of the above-described sterilizing device 1.

Furthermore, since the hand-disinfection sterilizing device 1C performs hand infection using sterilizing light, unlike a liquid-type hand disinfectant, the hand-disinfection sterilizing device 1C can be semi-permanently used without requiring frequent replacements, and the hand-disinfection sterilizing device 1C is capable of effectively disinfecting hands without causing discomfort such as sticky skin.

The operation of the above-described sterilizing device 1, 1A, 1B or 1C may be controlled through a wireless communication means such as a WIFI module of the controller 30 by executing an application, if the application is installed on a user's portable terminal.

The embodiments to be described below relate to an LED lighting device for sterilizing a surface or a space.

Figure 10:
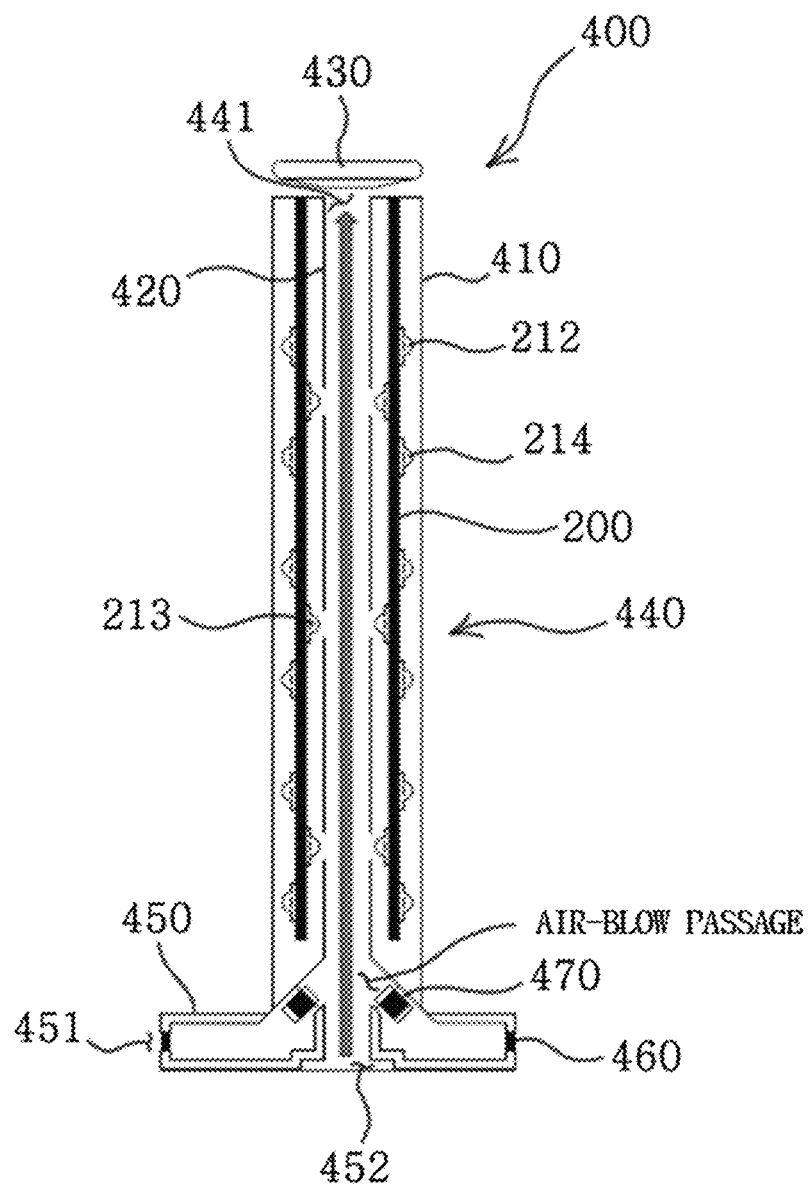
FIG. 10 is a schematic cross-sectional view of a light emitting diode (LED) lighting device for sterilizing a surface or a space.
Figure 11:
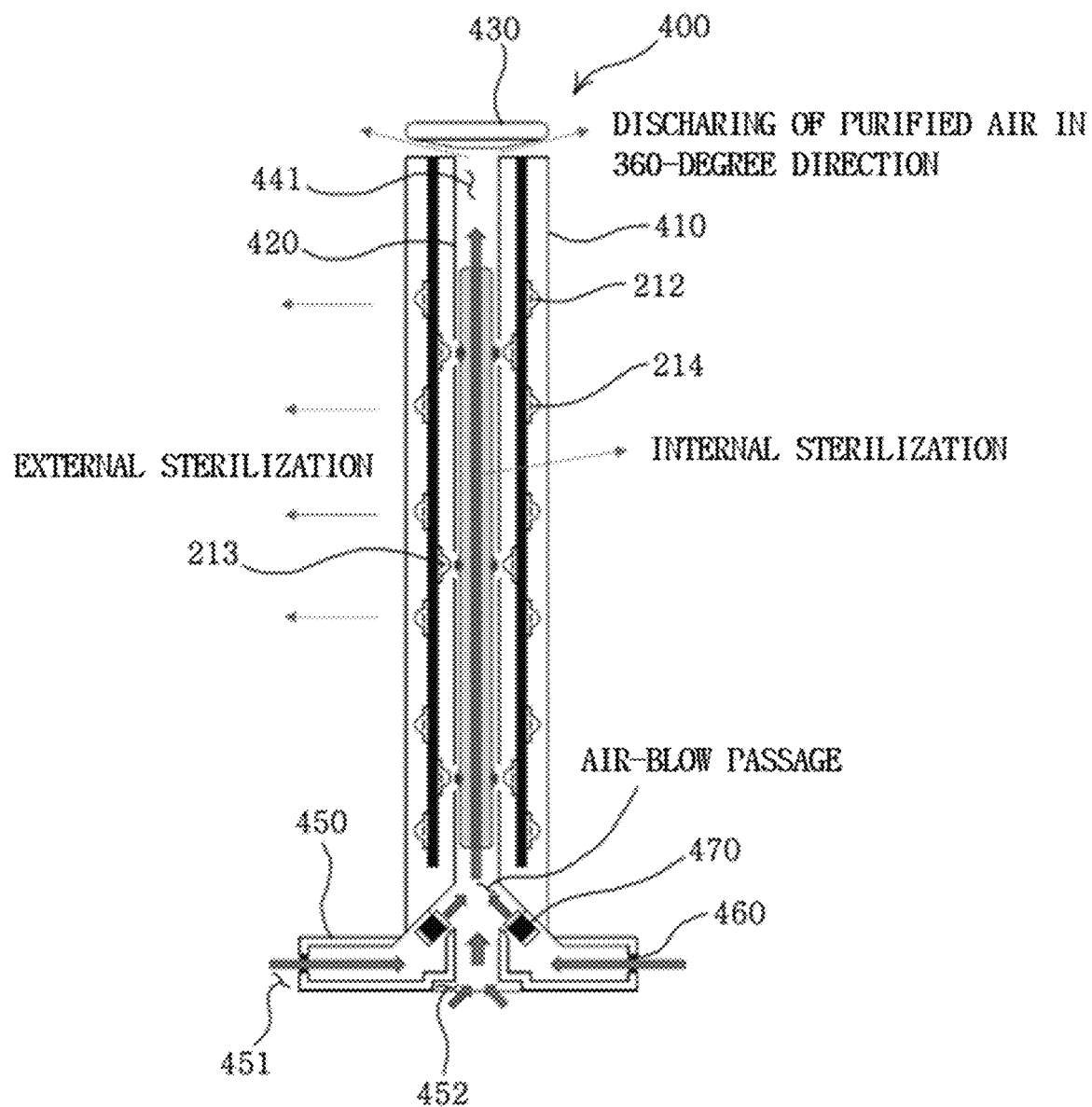
FIG. 11 is an operation state diagram of the LED lighting device for sterilizing a surface or a space of FIG. 10.

FIG. 10 is a schematic cross-sectional view of an LED lighting device for sterilizing a surface or a space, and FIG. 11 is an operation state diagram of the LED lighting device for sterilizing a surface or a space of FIG. 10.

As illustrated, the LED lighting device 400 for sterilizing a surface or a space includes an outer transparent tube 410, an inner transparent tube 420, a cover 430, a body 440, a stand 450, a filter 460, and a circulator 470.

The body 440 includes the outer transparent tube 410 and the inner transparent tube 420 in a double-tube type, while the inner transparent tube 420 is hollow to form a vertical ventilation hole 441, and a space is formed between the outer transparent tube 410 and the inner transparent tube 420. The substrate 200 is embedded in the space formed by the outer transparent tube 410 and the inner transparent tube 420.

That is, the body 440 is formed in the double-tube type, with the inner transparent tube 420 forming the vertical ventilation hole 441 and the outer transparent tube 410 spaced apart from the inner transparent tube 420 at a predetermined distance.

The first light emitting elements 212 and the second light emitting elements 214 are sequentially installed on an outer surface of the substrate 200 to be spaced apart from each other. As described above, the light of the first wavelength emitted by the first light emitting element 212 is visible light having a wavelength of 405 nm, and the light of the second wavelength emitted by the second light emitting element 214 is short-wavelength visible light having a wavelength in the range of 400 to 450 nm.

In addition, an ultraviolet lamp 213 is provided on an inner surface of the substrate 200 facing the vertical ventilation hole 441, and light emitted from the ultraviolet lamp 213 is ultraviolet light having a wavelength in the range of 207 to 222 nm.

The stand 450 is fixed to a lower surface of the body 440, with a hollow formed therein, and has a cross-sectional area wider than that of the body 440 to prevent the body 440 from falling down.

The stand 450 has a lower air inlet hole 452 penetrating through a lower surface thereof and a side air inlet hole 451 penetrating through a side surface thereof to allow external air to be introduced into. The introduced external air is discharged to an upper portion of the body 440 through an air-blow passage and the vertical ventilation hole 441.

The filter 460 is provided in the side air inlet hole 451 to eliminate foreign substances such as fine dust contained in air introduced from the outside.

Of course, the filter 460 may also be provided in the lower air inlet hole 452.

The cover 430 is spaced apart from an upper end of the body 440 at a predetermined distance, such that the purified air discharged from the vertical ventilation hole 441 is dispersed in a 360-degree direction.

A partition plate (not shown) is formed between a lower surface of the cover 430 and the upper end of the body 440 with the predetermined distance therebetween to fix the cover 430 to the upper end of the body 440 and to block the light from the body 440 from being emitted upwardly, thereby not only preventing the ultraviolet light from causing damage to the human body but also discharging the air in a 360-degree direction.

In addition, a display is formed on an upper surface of the cover 430 to display an on/off state of the sterilizing device, a contamination level of the surrounding environment, and the like, and a speaker is included to generate an alarm when the contamination level is a predetermined reference value or higher.

The circulator 470 is provided in the air-blow passage formed between the side air inlet hole 451 and the vertical ventilation hole 441 to allow external air introduced from the side air inlet hole 451 to be blown into the vertical ventilation hole 441.

The specific configuration of the circulator 470 will be described later.

The LED lighting device for sterilizing a surface or a space having the above-described structure further has an air purification function and effect by instantaneously sterilizing the air passing inside the LED lighting device for sterilizing a surface or a space using the ultraviolet light from the ultraviolet lamp 213, while performing sterilization with the light that is harmless to the human body outside the LED lighting device for sterilizing a surface or a space by effectively performing short-distance sterilization and long-distance sterilization by means of the light emitted from the first and second light emitting elements 212 and 214.

Hereinafter, the specific structure of the circulator will be described.

Figure 12:
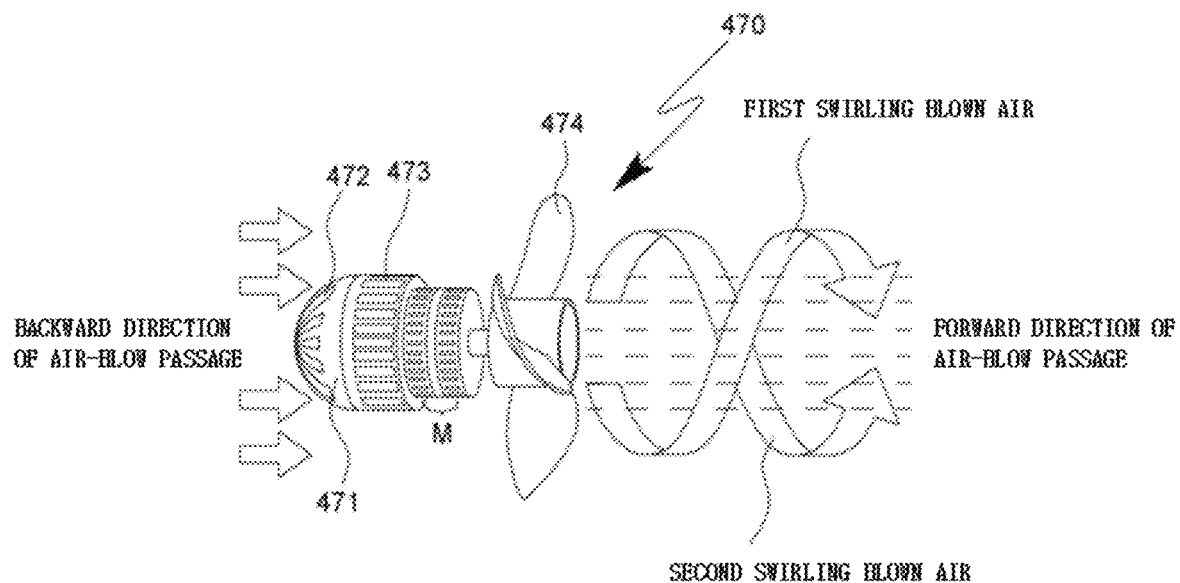
FIG. 12 is an external perspective view illustrating an operation state of a circulator.
Figure 13:
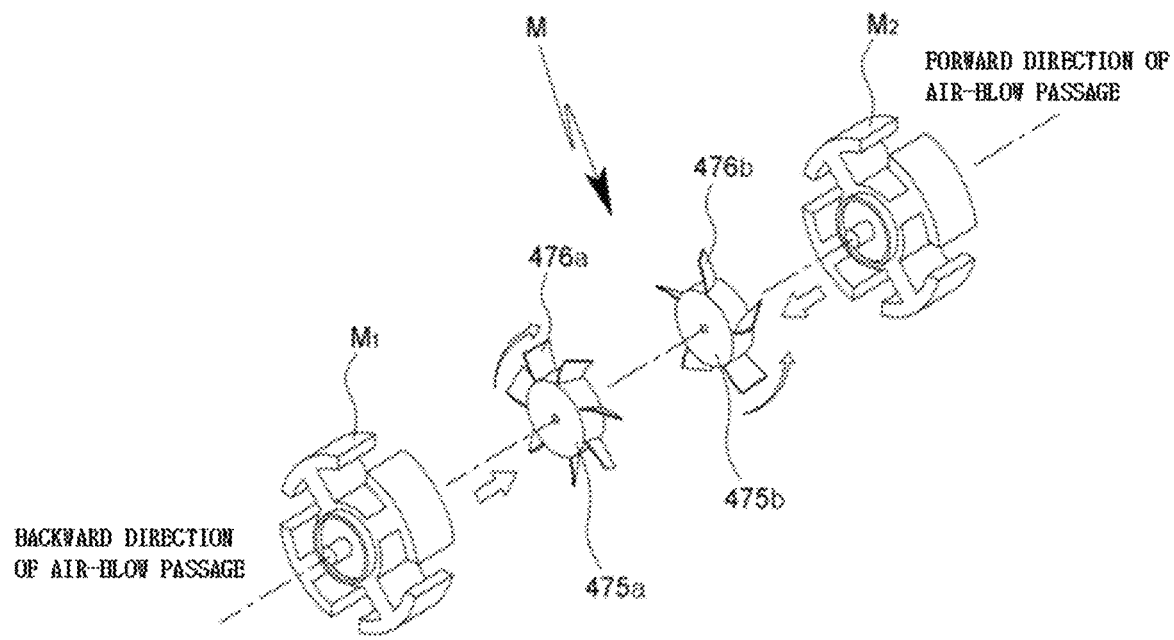
FIG. 13 is an enlarged exploded perspective view and an operation state diagram of a motor of FIG. 12.

FIG. 12 is an external perspective view illustrating an operation state of the circulator, and FIG. 13 is an enlarged exploded perspective view and an operation state diagram of a motor of FIG. 12.

As illustrated, the circulator 470 includes a housing 471, an inlet port 472, an outlet port 473, a fan 474, and a motor M.

The housing 471 has a cylindrical structure in which a space is formed to mount a component such as a motor therein.

The inlet port 472 is provided in a shape of a through hole passing through one end portion of the housing 471 to allow external air to be sucked thereinto.

The outlet port 473 is provided in a shape of a through hole passing through an outer surface of the housing 471 to discharge air compressed inside the housing 471 by the motor M, which will be described later.

The fan 474 is provided on one side of the motor M in a forward direction of the air-blow passage, and functions to blow the compressed air discharged from the outlet port in the forward direction of the air-blow passage.

The motor M is provided between the housing 471 and the fan 474, and includes a front brushless direct current (BLDC) motor M1, a rear BLDC motor M2, a first rotator 475a, a second rotator 475b, and first blade 476a, and a second blade 476b (see FIG. 12).

The BLDC motors M1 and M2, which are brushless motors each using an electronic circuit instead of a brush that is used in a conventional DC motor, are semi-permanent because they do not use a brush that is worn out more as used longer. The BLDC motors M1 and M2 are eco-friendly motors having a lifespan that is 10 times or more improved than the conventional DC motor, with an improvement in energy efficiency by 20% or more, while causing almost no noise and minimizing vibrations.

In addition, the fan 474 and the motor M are provided on a virtual coaxial line.

The front BLDC motor M1 is axially coupled to the first rotator 475a having a short cylindrical shape, and the first blade 476a is provided on an outer surface of the first rotator 475a with a predetermined inclination angle to generate first swirling blown air when rotated as the front BLDC motor M1 is driven.

The rear BLDC motor M2 is axially coupled to the second rotator 475b having a short cylindrical shape, and the second blade 476b is provided on an outer surface of the second rotator 475b with a predetermined inclination angle to generate second swirling blown air when rotated as the rear BLDC motor M2 is driven.

Here, one of the features of the present embodiment is that the first blade 476a is a 7-leaf blade and the second blade 476b is a 5-leaf blade, and the inclination angle of the first blade 476a and the inclination angle of the second blade 476b are formed in opposite directions.

In connection with the operation relationship based on the above-described circulator, when the motor M is driven, the front BLDC motor M1 and the rear BLDC motor M2 provided on the virtual coaxial line are rotated, and accordingly, the first rotator 475a operated in conjunction with the front BLDC motor M1 is rotated and the first blade 476a is rotated thereby, and the second rotator 475b operated in conjunction with the rear BLDC motor M2 is rotated and the second blade 476b is rotated thereby.

Since the inclination angle of the first blade 476a and the inclination angle of the second blade 476b are formed in opposite directions, the air from the first blade 476a and the air from the second blade 476b are blown in such a direction as to face each other, thereby forming the first swirling blown air and the second swirling blown air while the air is compressed by wind from the both sides.

At this time, since the first blade 476a is a 7-leaf blade, and the second blade 476b is a 5-leaf blade, the first swirling blown air and the second swirling blown air are directed in the forward direction of the air-blow passage while the compressed air is discharged through the outlet port 473 because the 7-leaf blade is stronger in pressure.

When the first swirling blown air and the second swirling blown air are directed in the forward direction of the air-blow passage, the fan 474, which is axially coupled to the rear BLDC motor M2, accelerates a wind speed of the blown air, such that the air is blown in the forward direction of the air-blow passage for the air to be blown from a lower side of the vertical ventilation hole 441 toward an upper side of the vertical ventilation hole 441.

The reason for applying the pressure to the blown air and forming the swirling air as described above is to maximize the sterilization effect.

That is, bacteria contained in the air may exist in a dense form by virtue of a carrier's saliva or the like. In this case, there is concern that when air containing a mass of bacteria in a dense state is introduced into the LED lighting device for sterilizing a surface or a space from the outside, the light irradiated from the ultraviolet lamp 213 may sterilize only an outer surface of the mass of bacteria while the air passes through the vertical ventilation hole 441 of the LED lighting device for sterilizing a surface or a space, and the efficiency may decrease in sterilizing the bacteria existing inside the mass of bacteria.

The present embodiment is to solve the above-described problem. By compressing the introduced air and forming the swirling air, the mass of bacteria contained in the air can be decomposed and diffused. Therefore, the ultraviolet light emitted from the ultraviolet lamp can be more accurately irradiated toward each bacterium, thereby maximizing the sterilization effect.

According to the present invention, the light can be emitted at different wavelengths to effectively perform short-distance sterilization or long-distance sterilization without causing damage to the human body, thereby maximizing the sterilization effect.

In addition, bacteria contained in circulating air can be sterilized to purify the air.

The present invention is not limited only to the above-described embodiments, and various modifications or changes may be made by those skilled in the art. The respective configurations, means, methods, or the like described in the embodiments provided above may be appropriately implemented either in combination or alone according to the need. Therefore, the scope of the present invention should be construed broadly to cover all aspects of embodiments and modifications including the technical configurations and equivalents thereto as defined by the appended claims.

What is claimed is:

1. A light emitting diode (LED) lighting device for sterilizing a surface or a space, the device comprising:
   a body including an inner transparent tube and an outer transparent tube in a double-tube shape, the inner transparent tube forming a vertical ventilation hole and the outer transparent tube being spaced apart from the inner transparent tube at a predetermined distance;
   a substrate provided in a space formed by the inner transparent tube and the outer transparent tube; and
   a first light emitting element and a second light emitting element provided on an outer surface of the substrate,
   wherein the first light emitting element emits visible light having a first wavelength of 405 nm, and
   the second light emitting element emits visible light having a second wavelength in a range of 400 to 450 nm.

2. The device of claim 1, wherein an ultraviolet lamp is provided on an inner surface of the substrate to face the vertical ventilation hole.

3. The device of claim 2, wherein the ultraviolet lamp emits ultraviolet light having a wavelength in a range of 207 to 222 nm.

4. The device of claim 3, wherein a circulator is provided in an air-blow passage formed between a side air inlet hole and the vertical ventilation hole.

5. The device of claim 4, wherein the circulator includes:
   a housing in which a space is formed;
   an inlet port provided in a shape of a through hole passing through one end portion of the housing to allow external air to be sucked thereinto;
   an outlet port provided in a shape of a through hole passing through an outer surface of the housing to discharge compressed air;
   a fan provided in a forward direction of the air-blow passage of the housing; and
   a motor provided between the housing and the fan.

6. The device of claim 5, wherein the motor includes a front brushless direct current (BLDC) motor and a rear BLDC motor.

7. The device of claim 6, wherein the front BLDC motor is axially coupled to a first rotator having a first blade provided on an outer surface thereof with a predetermined inclination angle, and
   the rear BLDC motor is axially coupled to a second rotator having a second blade provided on an outer surface thereof with a predetermined inclination angle.

8. The device of claim 7, wherein the inclination angle of the first blade and the inclination angle of the second blade are formed in opposite directions.

* * * * *